(12) United States Patent
Su et al.

(10) Patent No.: US 10,688,128 B2
(45) Date of Patent: Jun. 23, 2020

(54) USE OF Z-BUTYLIDENEPHTHALIDE IN ACTIVATING AUTOIMMUNE SYSTEM

(71) Applicant: EVERFRONT BIOTECH INC., New Taipei (TW)

(72) Inventors: Hong-Lin Su, Taichung (TW); Shinn-Zong Lin, Taichung (TW); Horng-Jyh Harn, New Taipei (TW); Tzyy-Wen Chiou, Hualien (TW); Sheng-Feng Tsai, Taichung (TW)

(73) Assignee: EVERFRONT BIOTECH INC., New Taipei (TW)

( * ) Notice: Subject to any disclaimer, the term of this patent is extended or adjusted under 35 U.S.C. 154(b) by 124 days.

(21) Appl. No.: 15/596,858

(22) Filed: May 16, 2017

(65) Prior Publication Data

US 2017/0333478 A1 Nov. 23, 2017

Related U.S. Application Data

(60) Provisional application No. 62/340,246, filed on May 23, 2016.

(51) Int. Cl.

| | | |
|---|---|---|
| *A61K 9/08* | (2006.01) | |
| *A61K 31/365* | (2006.01) | |
| *A61K 35/15* | (2015.01) | |
| *A61P 35/00* | (2006.01) | |
| *A61K 9/70* | (2006.01) | |
| *A61K 9/00* | (2006.01) | |

(52) U.S. Cl.
CPC ............ *A61K 35/15* (2013.01); *A61K 9/0019* (2013.01); *A61K 9/0085* (2013.01); *A61K 9/08* (2013.01); *A61K 9/7007* (2013.01); *A61K 31/365* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,662,899 A | 9/1997 | Chokri et al. | |
| 2006/0110469 A1* | 5/2006 | Luo | A61K 31/34 424/725 |
| 2010/0298427 A1* | 11/2010 | Fowler | A61K 31/343 514/470 |
| 2011/0165201 A1* | 7/2011 | Chiou | A61K 9/0024 424/400 |
| 2012/0178803 A1* | 7/2012 | Harn | A61K 31/343 514/473 |
| 2015/0352213 A1 | 12/2015 | Chiou et al. | |

FOREIGN PATENT DOCUMENTS

| | | |
|---|---|---|
| CN | 1943606 | 4/2007 |
| JP | 8-510118 | 10/1996 |
| JP | 2007082422 | 4/2007 |
| JP | 2012144512 | 8/2012 |
| JP | 2015229675 | 12/2015 |
| TW | 200616656 | 6/2006 |

OTHER PUBLICATIONS

Mitchell et al., Nature, vol. 519, pp. 366-369 (and 13 page method supplement); (published Mar. 19, 2015) (of record).*
Fu Bing-ji et al., Cellular immunotherapy of tumor; Journal of China Prescription Drug, Apr. 2007, 61:61-64. (English Translation).
Zhang Di, Study on the immune and pharmacological effects of Dang Gui (Angelica sinensis), Heilongjiang Science and Technology Information, Jun. 2014, p. 21. (English Translation).
International Search Report and Written Opinion of the International Searching Authority of International Patent Application No. PCT/CN2017/084455, dated Aug. 11, 2017.

\* cited by examiner

*Primary Examiner* — Soren Harward
*Assistant Examiner* — Paul D. Pyla
(74) *Attorney, Agent, or Firm* — Ping Wang; Morris, Manning & Martin LLP

(57) ABSTRACT

A method for at least one of activating autoimmune system and treating cancer is provided. The method comprises administering to a subject in need an effective amount of Z-butylidenephthalide and an effective amount of mononuclear cells.

12 Claims, 2 Drawing Sheets
(1 of 2 Drawing Sheet(s) Filed in Color)

though the PD-1 expression of T cells may easily result in an imbalance
USE OF Z-BUTYLIDENEPHTHALIDE IN ACTIVATING AUTOIMMUNE SYSTEM

FIELD OF THE INVENTION

The present invention relates to the use of Z-butylidenephthalide (Z-BP), especially relates to the use of Z-BP in activating autoimmune system. The effect of treating cancers by administering to a subject Z-BP in combination with mononuclear cells is much better than administering mononuclear cells alone.

BACKGROUND OF THE INVENTION

Regarding the treatment of cancers, in addition to the common therapeutic methods such as surgery, chemotherapy, radiation therapy and target gene therapy, immunotherapy has been considered as the most breakthrough anti-cancer strategy in recent years. Immunotherapy refers to that the autoimmune system is activated by an artificial manner, to recognize and attack cancer cells, so as to subject tumors to shrink or disappear and prolong patient's life span.

Clinical researches have shown that although immunotherapy shows quite good efficiency, some patients are insensitive to immunotherapy. For example, it was found in melanoma clinical researches that immune cells cluster around the tumor but cannot get into the tumor. In this respect, Dr. Tasuku Honjo and Dr. James P. Allison discovered that some cancer cells can induce immune cells to initiate a suppression of immune response through the surface antigen of cancer cells (e.g. PDL-1, CTLA-4), and thus both the autologous and exogenous immune cells cannot be activated. The surface antigen of cancer cells, such as programmed death-ligand 1 (PDL-1) and cytotoxic T lymphocyte associated protein 4 (CTLA-4), are also called immune checkpoint antigens.

To solve the above problems, Dr. Tasuku Honjo and Dr. James P. Allison collaboratively developed an antibody which is capable of neutralizing programmed death 1 (PD-1) on the surface of T cells, so as to disable the PDL-1 on the surface of cancer cells from binding to immune cells or further subjecting immune cells to die, and thus, can be used in therapy. However, it was found in a test that the block of PD-1 expression of T cells may easily result in an imbalance of immune cell regulatory mechanism in patients, and thus, result in patient's death. Therefore, some researchers think reversely to develop antibodies which can inhibit the expressions of immune checkpoint antigens on the surface of cancer cells for use in therapy.

For example, Ipilimumab is an immune checkpoint inhibitor. Results of the phase ill clinical trial showed that, with the administration of Ipilimumab alone, the overall survival rate of patients with stage three or four melanoma increased by 10.1 months, and that also proved the importance of immune checkpoints for cancer immunotherapy. However, the disadvantage in developing antibodies which can inhibit the expressions of immune checkpoint antigens is that the cost is quite high and the steps are complex. Therefore, there is a necessity and urgency for continuously developing a drug or method for inhibiting immune checkpoint antigens effectively.

Inventors of the present invention found that Z-BP is effective in inhibiting the expressions of immune checkpoint antigens of cancer cells, promoting cancer cells to secret chemokines capable of activating the immune system, increasing the amount of immune cells, and promoting the entry of immune cells into the tumor site, and thus, can be used for activating autoimmune system. Furthermore, inventors unexpectedly found that, the therapeutic efficacy of administering to a cancer subject Z-BP and mononuclear cells is much better than administering mononuclear cells alone.

SUMMARY OF THE INVENTION

An objective of the present invention is to provide a use of Z-BP in the manufacture of a medicament, wherein the medicament is used in combination with mononuclear cells for at least one of activating autoimmune system and treating cancer.

Another objective of the present invention is to provide a kit for immune cell therapy, comprising:
(1) a first part, comprising Z-BP; and
(2) a second part, comprising a mononuclear cell.
Wherein, the first part and the second part are administered simultaneously or separately to a subject.

Still another objective of the present invention is to provide a method for at least one of activating autoimmune system and treating cancer, comprising administering to a subject in need an effective amount of Z-BP and an effective amount of mononuclear cells.

The detailed technology and some particular embodiments implemented for the present invention are described in the following paragraphs for people skilled in this field to well appreciate the features of the claimed invention.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
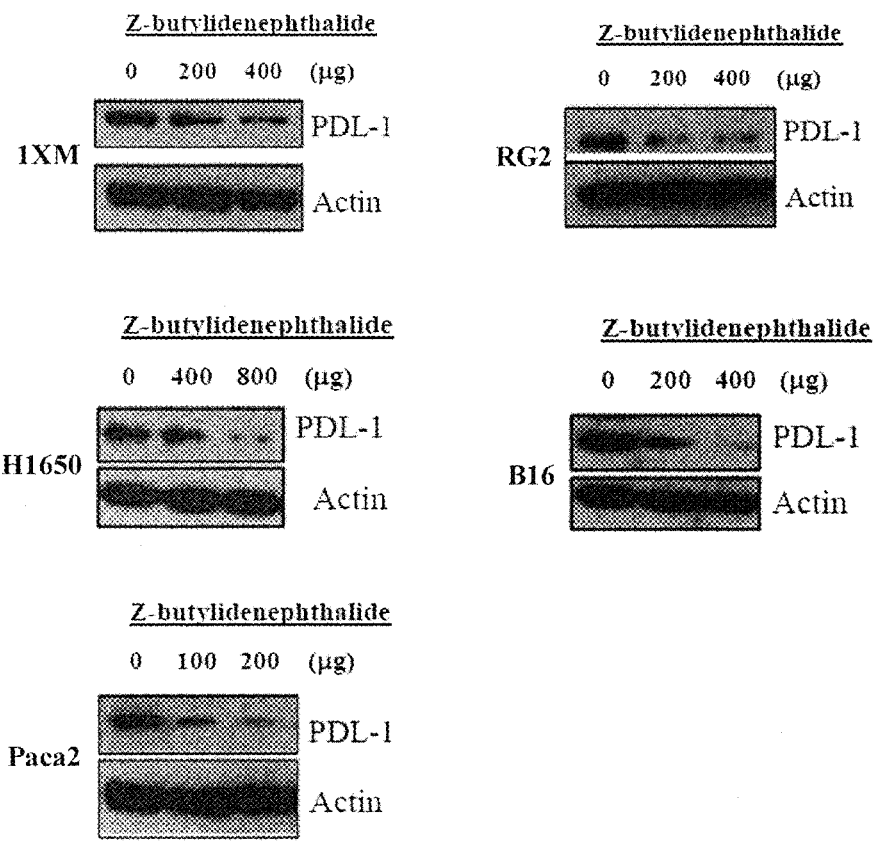
FIG. 1 is a group of pictures, showing the expressions of PDL-1 protein and actin of RG2 cell line, 1×M cell line, Paca2 cell line, H1650 cell line, and B16 cell line, wherein all the cell lines had been treated with different concentrations of Z-BP and the expressions were analyzed by Western Blotting.

The following will describe some of the embodiments of the present invention in detail. However, without departing from the spirit of the present invention, the present invention may be embodied in various embodiments and should not be limited to the embodiments described in the specification.

In addition, unless otherwise indicated herein, the expressions "a," "an," "the," or the like recited in the specification of the present invention (especially in the claims) are intended to include both the singular and plural forms. The term "treat" or "treating" used in this specification should not be construed as referring to treat a subject until the subject completely recovered, but should include maintaining the progression or symptoms of the diseases in a substantially static state, increasing the recovery rate of a subject, alleviating the severity of a particular condition, and increasing the quality of life of a patient. "Delay" or "delaying" the onset of a disease described in this specification refers to preventing the onset of a particular condition, and maintaining a sensitive subject in a healthy state or establishing a tolerance of the subject to a disease. The term "an effective amount" or "a therapeutically effective amount" used in this specification refers to the amount of the compound that can at least partially alleviate the condition that is being treated in a suspected subject when administered to the subject. The term "subject" used in this specification refers to a mammalian, including human and non-human animals. The unit "mg/kg-body weight" used in this specification refers to the dosage required per kg of body weight.

The numerical ranges (e.g., 5 to 100) used in this specification should be construed as including all of the rational numbers in the ranges and ranges consisting of any rational numbers in the ranges. Therefore, the numerical ranges used in this specification should include all the possible combinations of numerical values between the lowest value and the highest value listed therein. In addition, the word "about" as used herein substantially represents values within ±20% of the stated value, preferably within ±10% and more preferably within ±5%.

As described above, cancer cells can bind to immune cells through immune checkpoint antigens on their own surface to induce immune cells to initiate a suppression of immune response, and thus, can disable both autologous and exogenous immune cells from being activated and even lead immune cells to die. Therefore, if the expressions of immune checkpoint antigens of cancer cells can be effectively inhibited, the autoimmune system can be effectively activated and this would facilitate the use of immune cell therapy in treating cancers.

Inventors of the present invention found that Z-BP is effective in inhibiting the expressions of immune checkpoint antigens of cancer cells, promoting cancer cells to secret chemokines capable of activating the immune system, increasing the amount of immune cells, and promoting the entry of immune cells into the tumor site, and thus, can be used for activating autoimmune system and treating cancer in a combination with mononuclear cells. Inventors also unexpectedly found that the therapeutic efficacy of administering to a cancer subject Z-BP and mononuclear cells simultaneously is much better than administering to the subject mononuclear cells alone.

As shown in the examples provided hereinafter, in accordance with the present invention, it is believed that the use of Z-BP can activate autoimmune system of a subject that has been treated with a cancer immune cell therapy (i.e., a subject that has been administered with a mononuclear cell) or a subject that is ready to be treated with a cancer immune cell therapy (i.e., a subject being ready to be administered with a mononuclear cell), and thus, can enhance the efficiency of the immune cell therapy.

Therefore, the present invention provides the use of Z-BP in activating autoimmune system, comprising the use of Z-BP in the manufacture of a medicament for use in combination with mononuclear cells, providing a kit comprising Z-BP and a mononuclear cell, and the method for activating autoimmune system and treating cancer comprising administering Z-BP and mononuclear cells to a subject in need.

In the use of the present invention, autologous and/or exogenous mononuclear cells such as lymphatic cells, myeloid cells, phagocytes, antigen presenting cells could be used. In particular, the examples of mononuclear cells include T cells, B cells, NK cells, mast cells, basophilic granulocytes, acidophilic granulocytes, neutrophils, macrophages, and dendritic cells, but is not limited thereby.

Depending on the purpose, the mononuclear cell adopted by the use of the present invention could be administered to a subject in need in any suitable form without specific limitations. For example, the mononuclear cell could be administered to a subject in need by corticospinal tract injection, intrathecal injection, intracerebral injection, intravenous injection, peritoneal injection, and/or subcutaneous injection, but the administration is not limited thereby. In some embodiments of the present invention, the mononuclear cell could be administered in a form of intravenous injection.

The medicament provided according to the use of the present invention could be administered to any cancer cell which is capable of expressing immune checkpoint antigens. Without being limited by the theory, it is believed that the medicament could increase the amount of immune cells in cancer patients and promote the entry of immune cells into the tumor site by inhibiting the expressions of immune checkpoint antigens on the surface of cancer cells, and thus, achieve the effect of eliminating cancer cells. In some embodiments of the present invention, the medicament provided according to the use of the present invention is used for inhibiting the expressions of immune checkpoint antigens of one or more cancer cell(s) as follows: malignant brain tumor cells, malignant glioblastoma stem cells, pancreatic cancer cells, lung cancer cells, and melanocytoma cells.

Depending on the purpose, the medicament according to the use of the present invention could be provided in any suitable form without specific limitations. For example, the medicament could be administered by an oral or parenteral (such as transdermal administration, nasal administration, subcutaneous injection, intravenous injection, muscular injection, peritoneal injection, subcutaneous implantation or interstitial implantation) route to a subject in need to activate autoimmune system and enhance the efficiency of cancer immune cell therapy, but the administration is not limited thereby. Depending on the form and purpose, suitable carriers could be chosen and used to provide the medicament, as long as the carriers do not adversely affect the desired effects of Z-BP and/or mononuclear cells, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form suitable for oral administration, examples of the carrier include, but are not limited to, water, saline, dextrose, glycerol, ethanol or its analogs, cellulose, starch, sugar bentonite, and combinations thereof. The medicament could be provided in any suitable form for oral administration, such as in a solid form (such as in the form of a tablet, a pill, a capsule, granules, a pulvis), or in a liquid form (such as in the form of an oral liquid, a syrup, a spirit, an elixir, a tincture), etc., but the form is not limited thereby.

As for the form of injection or drip suitable for subcutaneous, intravenous, muscular, or peritoneal administration, the medicament provided by the present invention could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the medicament as an intravenous infusion, an emulsified intravenous infusion, a powder for injection, a suspension for injection, or a powder suspension for injection, etc. Alternatively, the medicament could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need. Furthermore, as for the external dosage form for nasal or transdermal administration, the medicament could be provided in the form of, for example, a liniment (such as an emulsion, a cream, a gel, a dispersing paste, an ointment), a spray, a patch, or a solution (such as a cleaning liquid, a suspension).

As a dosage form suitable for subcutaneous implantation or interstitial implantation, the medicament provided by the present invention could further comprise one or more ingredient(s), such as an excipient, a stabilizer, a buffer, other carriers, etc., to prepare the medicament in a form of, for example, a wafer, a tablet, a pill, a capsule, etc. Therefore, the medicament could be implanted into a subject, and the active ingredients contained therein could slowly and continuously be released to the surrounding tissue, and thus, could achieve a locally stable high dose of medicament and the effect of activating autoimmune system could be provided thereby. For example, the medicament provided by the present invention could comprise a biocompatible polymer to prepare the medicament in the form of a wafer for subcutaneous implantation or interstitial implantation, but is not limited thereby. The biocompatible polymer could be commercially available or be prepared by a known synthetic process in the field of the present invention. In some embodiments of the present invention, a polyanhydride, such as p(CPP-SA) copolymer provided by bis (p-carboxylphenoxy) propane and sebacic acid, is used as the biocompatible polymer.

In the medicament provided according to the use of the present invention, the ratio of Z-BP in the medicament could be adjusted depending on practical requirements. For example, the weight percentage of Z-BP could range from about 1% to about 40%, and preferably from about 2% to about 30%, based on the total weight of the medicament. In some embodiments of the present invention, the medicament is provided in the form of a wafer (i.e., Cerebraca wafer), and the weight percentage of Z-BP in the wafer is about 25%.

Optionally, the medicament provided by the present invention could further comprise a suitable amount of additives, such as a flavoring agent, a toner, or a coloring agent for enhancing the palatability and the visual perception of the medicament, and a buffer, a conservative, a preservative, an antibacterial agent, or an antifungal agent for improving the stability and storability of the medicament. In addition, the medicament could optionally further comprise one or more other active ingredient(s), or be used in combination with a medicament comprising one or more other active ingredient(s), to further enhance the effect of the medicament, or to increase the application flexibility and adaptability of the preparation thus provided, as long as the other active ingredients do not adversely affect the desired effects of Z-BP and/or the mononuclear cells.

To ensure that the medicament provided by the present invention could provide the desired efficacy of activating autoimmune system in a subject, the medicament could be administrated to the subject prior to, after, or along with administering mononuclear cells to the subject, so as to enhance the efficiency of immune cell therapy. In the aforementioned immune cell therapy, mononuclear cells could be administered at an amount preferably ranging from about $1\times10^2$ to about $1\times10^{10}$ cells/injection site each time, and more preferably about $1\times10^5$ to about $1\times10^7$ cells/injection site each time. Depending on the need, age, body weight, and health conditions of the subject, the medicament provided by the present invention and mononuclear cells could be dosed separately at various administration frequencies, such as once a day, multiple times a day, or once every few days, etc.

For example, when the medicament provided by the present invention is administered by interstitial implantation to a subject that has been treated with an immune cell therapy, or a subject that is ready to be treated with an immune therapy to activate autoimmune system of the subject, the dosage of the medicament is about 30 mg/kg-body weight to about 2000 mg/kg-body weight per day, preferably about 100 mg/kg-body weight to about 1,000 mg/kg-body weight per day, and more preferably about 200 mg/kg-body weight to about 500 mg/kg-body weight per day, based on the total weight of Z-BP. However, for acute patients, the dosage of the mononuclear cells and the medicament provided according to the present invention could be optionally increased, for example, up to several folds or dozen folds, depending on the practical requirements.

In some embodiments of the present invention, the medicament provided according to the present invention is used in combination with mononuclear cells for treating brain cancer, wherein the medicament is administered in the form of a wafer and by interstitial implantation, and the mononuclear cell is administered by injections.

The present invention also provides a kit in immune cell therapy, comprising (1) a first part, comprising Z-BP; and (2) a second part, comprising a mononuclear cell. In particular, the first part is the above medicament provided according to the present invention. The form, applied frequency, and dosage range of the first part and the second part are all in line with the above description.

The kit according to the present invention could further comprise a third part comprising a solvent or a solution, wherein, prior to being used, the solvent or solution could be mixed with the first part and/or the second part to provide an injection solution.

The solvent suitable for being used as the third part include, but are not limited to a polar solvent, such as water, dimethyl sulfoxide (DMSO), ethanol, etc. The solution suitable for being used as the third part include, but are not limited to a salt-buffered saline and any suitable injection solution used for providing for injection forms. The examples of salt-buffered saline include, but are not limited to, phosphate-buffered saline (PBS), citrate-buffered saline, physiological saline, etc.

In some embodiments of the kit of the present invention, the kit comprises a first part, a second part, and a third part, wherein the first part is provided as a form of wafer, the second part (comprising the mononuclear cell) was mixed with the third part to provide an injection solution prior to being administered to a subject, and the third part is preferably PBS.

Each part in the kit of the present invention is generally packaged and stored separately, and also could be transported, sold separately or in a set. When each part in the kit of the present invention is packaged and stored separately, and each component of the kit is transported and sold separately, the first part is preferably kept in a dark environment with a temperature below 4□, and the second part is preferably kept in an environment with a temperature below −80□. Also, if each component of the kit in the present invention is transported and sold in a set, the first part, the second part, and the third part could be kept separately in a container with an interior temperature of below 4□, a container with an interior temperature of −80□ (e.g., a liquid nitrogen tank), and a container with an interior temperature of −20□ (e.g., an ice box). There is no specific limitation for the shape and the size of each container, as long as the interior of each container is isolated from the exterior temperature so that all the parts could be transported and sold in a set without affecting the preservation temperature of each other.

Any suitable frozen liquid could be used in the preservation of the second part, as long as the composition of the frozen liquid could maintain the survival rate of the second part (comprising the mononuclear cell) effectively. Usually, the composition of the frozen liquid is adjusted depending on the corresponding second part (comprising the mononuclear cells). In general, the composition of the frozen liquid includes DMSO, nutritional components (e.g., glucose), pH adjusting agent, etc.

The kit according to the present invention could further comprise a user instruction manual for the user to optionally adjust the applied manner, applied frequency, and applied dosage of each part.

The present invention also provides a method for activating autoimmune system and treating cancer, comprising administering to a subject in need an effective amount of Z-BP and an effective amount of mononuclear cells, wherein the administration of Z-BP and the administration of mononuclear cells could be carried out simultaneously or separately. Preferably, the method of the present invention is for treating cancer, wherein the cancer is at least one of malignant brain tumor, glioblastoma, pancreatic cancer, lung cancer, and melanocytoma. The applied manner, applied frequency, and dosage range of the mononuclear cells are all in line with the above description. As for Z-BP, it could be used as a form of the medicament provided according to the present invention, but is not limited thereby.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Example 1: Effect of Z-BP on Inhibiting the Expressions of Immune Checkpoint Antigens of Cancer Cells As described above, PDL-1 is an immune checkpoint antigen expressed on the surface of cancer cells, can bind to immune cells and induce immune cells to initiate a suppression of immune response, and thus, can disable both autologous and exogenous immune cells from being activated and even subject immune cells to die.

The RG2 cell line (rat malignant glioma cells), 1×M cell line (glioblastoma stem cells), Paca2 cell line (human pancreatic cancer cells), 1-11650 cell line (human non-small-cell lung cancer cells), or B16 cell line (mouse melanocytoma cells) were independently treated with various concentrations of Z-BP for 24 hours. Then, the proteins in the cells were extracted and the expressions of PDL-1 protein in the cancer cells treated with Z-BP were detected by Western Blotting. In addition, the expression of actin was detected and used as the internal control. The results are shown in FIG. 1.

As shown in FIG. 1, the expressions of PDL-1 proteins in RG2 cell line, 1×M cell line, Paca2 cell line, H1650 cell line, and B16 cell line all significantly decreased along with the increment in the concentration of Z-BP. These results show that Z-BP is effective in inhibiting the expressions of immune checkpoint antigens of cancer cells, so that can block the binding between cancer cells and immune cells, and thus, can be used for enhancing the efficiency of cancer immune cell therapy.

Example 2: Use a Combination of Z-BP and Mononuclear Cells to Treat Cancer (2-1) Preparation of Mononuclear Cells 10 ml whole blood was collected from the experimental rats by cardiac puncture and placed into a blood collection tube (purchased from BD Vacutainer, number: 367988) to be centrifuged by 500-1800 g for 15 minutes. Then, the supernatant was removed and the mononuclear cell layer was placed into another centrifuge tube.

Thereafter, the mononuclear cells (i.e., peripheral blood mononuclear cell, PBMC) were diluted with PBS to a concentration of $1\times10^6$ cells/100 µl for the following experiments.

(2-2) Establishment of Animal Models

Twenty four F344 rats were subject to an inhalational anesthesia with 1.5-2% isoflurane gas, and then a 2 mm hole was drilled from the brain of each rat. Thereafter, RG2 cell fluid ($1\times10^5$ cells/10 l/each rat) was injected into corpus striatum of rat, and then the hole was sutured, so that an in situ malignant brain glioblastoma animal model was established. After three days, a hole with the previous drilled hole as the center and a radius of 10 mm was drilled, and then the rats were randomly divided into four groups (6 rats in each group) and treated as follows to carry out subsequent experiments:

(1) "Empty wafer" group: a wafer containing no active component (provided by EVERFRONT BIOTECH INC.) was placed into the brain of each rat.

(2) "Empty wafer+PBMC" group: a wafer containing no active component was placed into the brain of each rat, and then $1\times10^6$ PBMC obtained from (2-1) was administered to each rat via caudal intravenous injection.

(3) "Cerebraca wafer" group: a wafer containing Z-BP (7.5 mg Z-BP/wafer; provided by EVERFRONT BIOTECH INC.) was placed into the brain of each rat.

(4) "Cerebraca wafer+PBMC" group: a wafer containing Z-BP (7.5 mg Z-BP/wafer) was placed into the brain of each rat, and then $1\times10^6$ PBMC obtained from (2-1) was administered to the rat via caudal intravenous injection.

(2-3) Observation of the Survival Situation

The survival situation of the rats of each group was daily observed and recorded. The results are shown in FIG. 2 and Table 1.

TABLE 1

| Groups | Average survival days | Median survival time |
|---|---|---|
| "Empty wafer" group | 19.1 ± 2.15 | 19 |
| "Empty wafer + PBMC" group | 23.2 ± 2.95 | 25 |
| "Cerebraca wafer" group | 34.1 ± 3.8 | 34 |
| "Cerebraca wafer + PBMC" group | 44 ± 6 | 43 |

Figure 2:
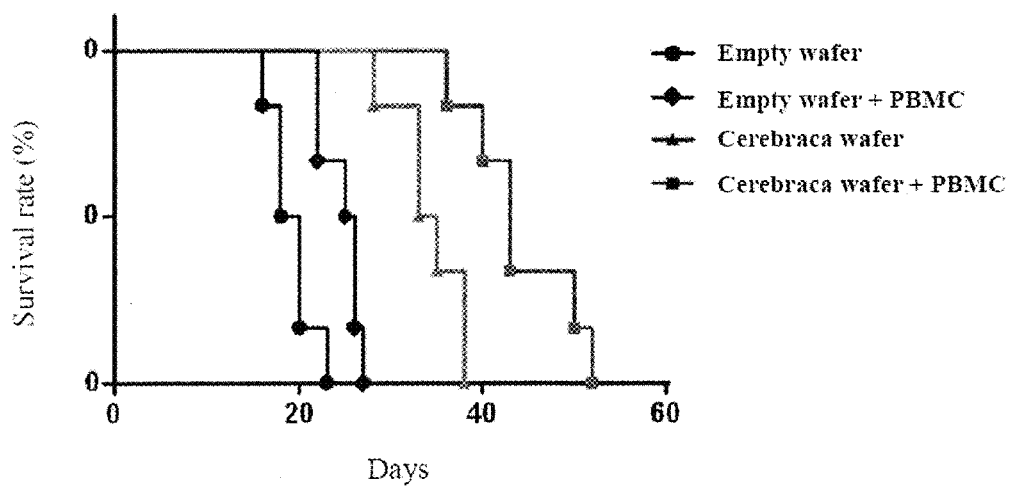
FIG. 2 is a curve diagram, showing the survival rate of rats which have been treated with different conditions, wherein "empty wafer" refers to the control group treated only with a wafer containing no active component, "empty wafer+PBMC" refers to the group treated with a wafer containing no active component in combination with mononuclear cells, "Cerebraca wafer" refers to the group treated only with a Z-BP-containing wafer, and "Cerebraca wafer+PBMC" refer to the group treated with a Z-BP-containing wafer in combination with mononuclear cells.

As shown in FIG. 2 and Table 1, as compared to the "empty wafer" group, the life span of the rats in the "empty wafer+PBMC" group, "Cerebraca wafer" group, and "Cerebraca wafer+PBMC" group prolonged by about 6, 15, and 24 days, respectively. These results show that the life span of a subject with malignant brain tumor that is administered with mononuclear cells alone could be prolonged, and the subject with malignant brain tumor that is administered with Z-BP in combination with mononuclear cells could be prolonged more effectively.

(2-4) Observation of Immune Cells

After the rats of (2-3) were dead, their brains were collected to prepare the pathological tissue slices. Then, the pathological tissue slices were subjected to immunohistochemistry (IHC) with CD4, CD8, CD11b, and CCL20 antibodies (purchased from Genetex company) at the tumor site, and observed through a microscope. The results are shown in FIG. 3.

Figure 3:
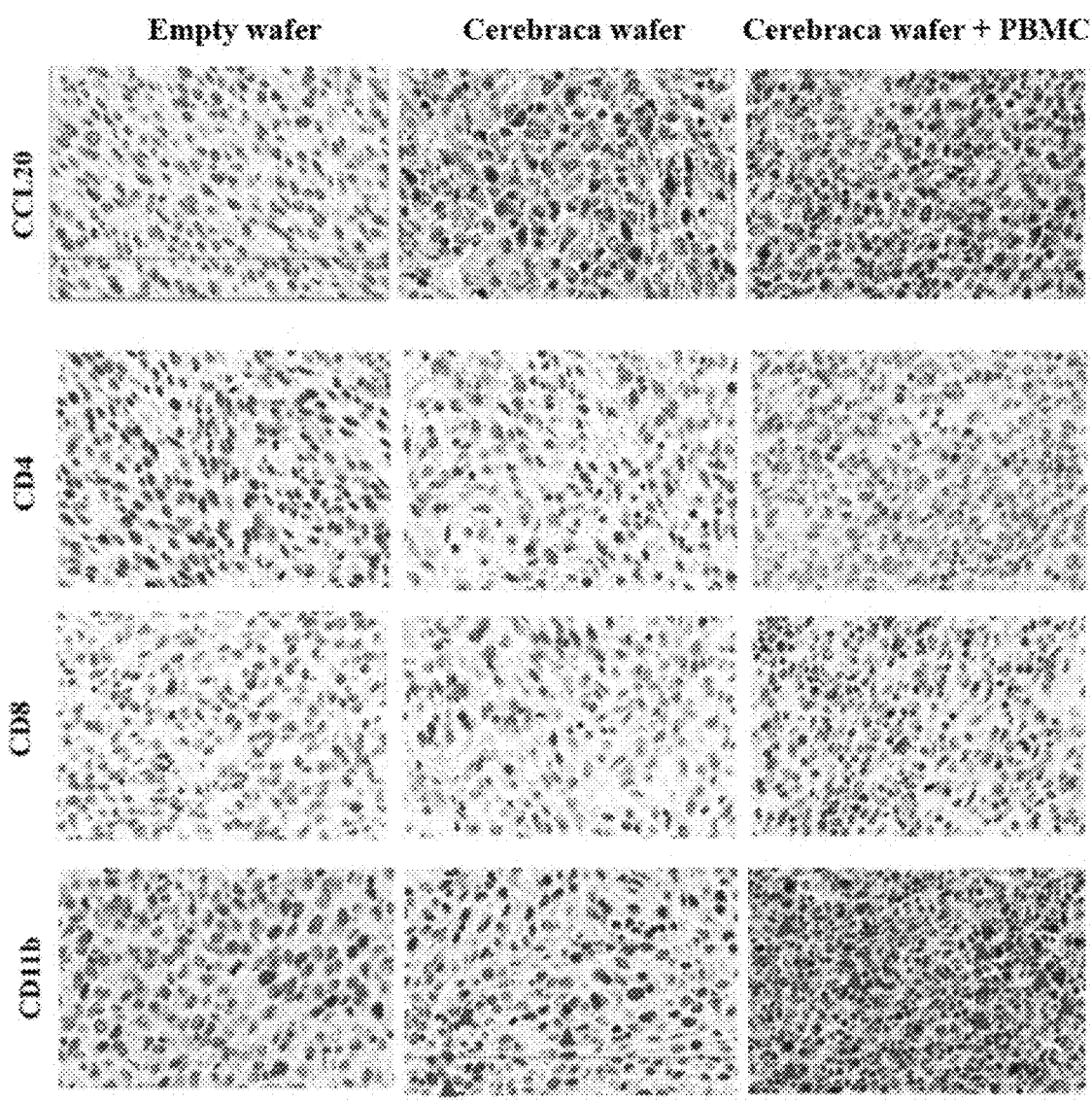
FIG. 3 is a group of pictures, showing the brain tissues of rats of the "empty wafer" group, "Cerebraca wafer" group, and "Cerebraca wafer+PBMC" group, wherein the brain tissues were analyzed by immunohistochemistry.

As shown in FIG. 3, as compared to the "empty wafer" group, CCL20 (a chemokine secreted by cancer cells and has the function of attracting immune cells) at the tumor site of the rats in the "Cerebraca wafer" group was trending increased, and the increasing trend of CCL20 at the tumor site of the rats in the "Cerebraca wafer+PBMC" group was more significant.

On the other hand, as compared to the "empty wafer" group, the number of $CD4^+$ T cells, $CD8^+$ T cells, and $CD11b^+$ cells (i.e., dendritic cells) at the tumor site of the rats of the "Cerebraca wafer" group were also trending increased, and the increasing trend of the number of $CD4^+$ T cells, $CD8^+$ T cells, and $CD11b^+$ cells at the tumor site of the rats in the "Cerebraca wafer+PBMC" was more significant.

The above results show that Z-BP is effective in promoting cancer cells to secret chemokines capable of activating immune system, increasing the amount of immune cells, and promoting the entry of immune cells into the tumor site. In addition, a combination of Z-BP and mononuclear cells can further enhance the efficiency of the aforementioned effects.

As the results shown in the aforementioned cellular and animal experiments, Z-BP can activate autoimmune system effectively and subject immune cells to successfully recognize and kill cancer cells, and thus, can be used in combination with mononuclear cells in the treatment of cancer to enhance the efficiency of cancer immune cell therapy.

BRIEF DESCRIPTION OF REFERENCE NUMERALS

Not applicable.

What is claimed is:

1. A method for activating autoimmune system, comprising administering to a subject for inhibition of expression of immune checkpoint antigens of cancer cells an effective amount of Z-butylidenephthalide (Z-BP) and an effective amount of mononuclear cells.

2. The method as claimed in claim 1, wherein the mononuclear cell is selected from the group consisting of an autologous mononuclear cell, an exogenous mononuclear cell, and combinations thereof.

3. The method as claimed in claim 1, wherein the mononuclear cell is at least one of peripheral blood mononuclear cell (PBMC), lymphatic cell, myeloid cell, phagocyte, and antigen presenting cell.

4. The method as claimed in claim 1, wherein the mononuclear cell is at least one of T cell, B cell, NK cell, mast cell, basophilic granulocyte, acidophilic granulocyte, neutrophil, macrophage, and dendritic cell.

5. The method as claimed in claim 1, wherein Z-BP is administered to the subject by oral administration, transdermal administration, nasal administration, subcutaneous injection, intravenous injection, intramuscular injection, peritoneal injection, subcutaneous implantation, interstitial implantation, or two or more of the aforementioned administrations.

6. The method as claimed in claim 5, wherein Z-BP is administered to the subject as a wafer.

7. The method as claimed in claim 1, which is for treating cancer, wherein the cancer is at least one of malignant brain tumor, glioblastoma, pancreatic cancer, lung cancer, and melanocytoma.

8. The method as claimed in claim 1, wherein Z-BP is administered at an amount ranging from about 30 mg/kg-body weight to about 2,000 mg/kg-body weight per day.

9. The method as claimed in claim 8, wherein Z-BP is administered at an amount ranging from about 100 mg/kg-body weight to about 1,000 mg/kg-body weight per day.

10. The method as claimed in claim 7, wherein Z-BP is administered at an amount ranging from about 30 mg/kg-body weight to about 2,000 mg/kg-body weight per day.

11. The method as claimed in claim 10, wherein Z-BP is administered at an amount ranging from about 100 mg/kg-body weight to about 1,000 mg/kg-body weight per day.

12. The method as claimed in claim 1, wherein the immune checkpoint antigen is at least one of PDL-1 and CTLA-4.

* * * * *